United States Patent [19]

Lundmark

[11] Patent Number: 4,675,068
[45] Date of Patent: Jun. 23, 1987

[54] ARRANGEMENT FOR BONDING AN ELASTIC RIBBON TO A PLASTICS WEB WITH THE AID OF AN ADHESIVE

[75] Inventor: Einar Lundmark, Balsta, Sweden

[73] Assignee: Mo och Domsjo Aktiebolag, Sweden

[21] Appl. No.: 790,012

[22] Filed: Oct. 22, 1985

[30] Foreign Application Priority Data

Nov. 28, 1984 [SE] Sweden ................................. 8405999

[51] Int. Cl.⁴ ........................ B32B 31/08; B65H 23/04
[52] U.S. Cl. .................................... 156/495; 156/164; 156/494; 156/497; 156/549; 156/554
[58] Field of Search ............... 156/164, 229, 497, 494, 156/495, 549, 554; 29/121.1, 121.4, 121.5; 269/21

[56] References Cited

U.S. PATENT DOCUMENTS 2,782,574  2/1957  Copold ................................. 269/21
3,828,367  8/1974  Bourgeois ........................... 156/164
4,207,998  6/1980  Schmid ............................... 29/121.1
4,360,398  11/1982  Sabee .................................. 156/164
4,479,836  10/1984  Dickover et al. .................... 156/164

FOREIGN PATENT DOCUMENTS

0027303  7/1983  European Pat. Off. .

Primary Examiner—Donald E. Czaja
Assistant Examiner—J. Davis
Attorney, Agent, or Firm—Sughrue, Mion, Zinn, Macpeak, and Seas

[57] ABSTRACT

The invention relates to an arrangement for bonding an elastic ribbon (51) under tension to a plastics web (10) along a curved path thereon with the aid of an adhesive, in the manufacture of diapers or like articles. The ribbon is introduced into a given cured path on a cylindrical drum (15). Arranged in the given path are suction openings which communicate with a suction source and are effective in holding the ribbon firmly by suction along the whole of its length, therewith preventing the ribbon from sliding relative to the drum and the plastics web and from twisting or tilting on the drum despite the tension in the ribbon. Means (89) are provided for breaking the connection between the suction openings and the suction source as the suction openings pass the end point of a given distance on the drum (15).

16 Claims, 12 Drawing Figures

ARRANGEMENT FOR BONDING AN ELASTIC RIBBON TO A PLASTICS WEB WITH THE AID OF AN ADHESIVE

The present invention relates to an arrangement for bonding a tensioned elastic ribbon with the aid of an adhesive along a given path on a plastics web in the manufacture of diapers or similar liquid-absorbing products, specifically the ribbon is introduced by feed-in means onto a rotatable cylindrical drum driven by drive means in correspondence with the given path, and the ribbon is brought together with the plastics web which is moved through a given distance on the peripheral surface of the drum. In the peripheral surface of the drum, an array of suction openings are provided in correspondence with the given path, and which suction openings communicate with a suction source in a manner to retain the ribbon in its position on the peripheral surface of the drum. Means for breaking the connection between the suction openings and the suction source as a respective suction opening completes its passage along said path are also provided.

Such an arrangement is known from EP-A-No. 108 173. In this known arrangement the tensioned ribbon is placed along a straight path on the periphery of the drum and the ends of the ribbon are drawn firmly against the drum periphery by suction, so that the ribbon is held stretched and in contact with the plastics web until the adhesive has hardened. A serious drawback with this known arrangement is that the ribbon is under uniform tension along the whole of its length, and that consequently the plastics web is gathered uniformly along the whole length of the resultant diaper or like absorbent. It is desirable to achieve a variable ribbon tension, so that gathering of the diaper or like absorbent is more pronounced in the crotch part thereof, as described for example in EPC-Patent publication No. 0 027 303. The arrangement described in this patent specification No. 0 027 303 lacks means for holding the ribbon in tension, and consequently there is a danger that the ribbon will contract relative to the plastics web before the adhesive has completely hardened, which results in equalization of the tension along the whole of the ribbon, this problem being particularly serious when the greatest tension is located at the central part of the ribbon, coinciding with the crotch part of the diaper. Moreover, in the manufacture of diapers the greatest possible effort is made to arrange the elastic ribbons so that they follow the shape of the body to the greatest possible extent, partly to obtain the best possible sealing effect and partly so that the diaper is comfortable to wear. This necessitates placing the ribbon along a curved path on the drum, which then creates the problem of the ribbon twisting or tilting due to the fact that the width of a normal ribbon is greater than its thickness. Such twisting or tilting of the ribbon results in poor adhesion between the plastics web and the ribbon. Consequently, in order to enable ribbons to be attached along curved paths the use of ribbons of substantially circular cross-section has been proposed, as disclosed in U.S. Pat. No. 3,828,367 for example.

Accordingly, the main object of this invention is to provide an arrangement of the kind described in the introduction which will enable ribbons to be attached along curved paths and which will permit such ribbons to have varying tension over the whole of the bonding area.

This main object is realized fully with the arrangement according to the invention described hereinafter with reference to an embodiment thereof illustrated in the accompanying drawings, in which.

Figure 1:
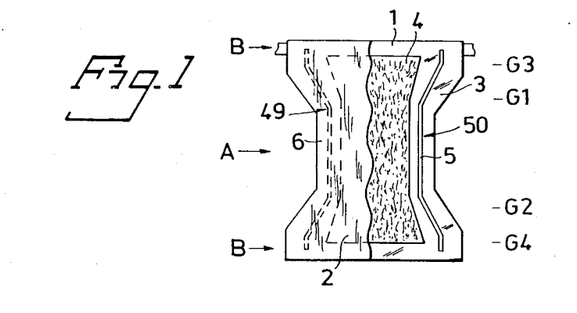
FIG. 1 illustrates a type of diaper incorporating curved elastic ribbons.

In order to facilitate an understanding of the invention there is shown in FIG. 1 an embodiment of a diaper of hour-glass configuration which has been chosen by way of example only and which has been provided with elastic tape in the crotch and side portions thereof so that when being worn, the diaper will be sealed as tightly as possible against the body.

The disposable diaper 1 illustrated in FIG. 1 comprises a liquid-permeable inner layer 2 of nonwoven material or the like, i.e. a layer which faces the body of the wearer, and an impervious outer layer or topsheet 3 made of plastics film or plastics foil. Arranged between the layers 2 and 3 is a liquid absorbent pad 4 of fluffed cellulose or like material. Elastic curved ribbons or filaments 5 are incorporated in the mutually joined side portions or panels 6 of the two layers 2 and 3, these side portions lying outside the pad 4. In the illustrated embodiment the ribbons or filaments 5, which are made of rubber or like material for example, are attached to the plastics web 3 in curved lines with the aid of an adhesive. Prior to attaching the ribbons 5, they are stretched so that after being firmly bonded to the plastics web they draw together at the crotch part A of the diaper and, if desired, also at the side parts B thereof, so that the edges of the diaper are gathered together, thereby to seal more efficiently against the body of the wearer. The stretched elastic ribbons 5 are laid along the outer contours of the diaper. Although not shown, each diaper may be provided with an elastic waist band firmly adhered to the two end parts of the outer plastics foil.

It will be assumed hereinafter that the elastic ribbons comprise thin rubber ribbons which are bonded to the plastics web with a hot-melt adhesive, although it will be understood that the elastic ribbons may comprise any suitable materials whatsoever, such as, for example, an ethylene-propylene-rubber mixture (EPR) with an ethylene vinyl acetate extruded into thin ribbons which are stretched while applying heat thereto. The stretched ribbon is then cooled and remains stretched while retaining its elasticity. When subsequently heated the ribbon returns to its original length.

The hot-melt adhesive can be replaced, for example, with double-sided adhesive foil, one surface of which adheres to the ribbon and the other surface of which is brought together with the aforesaid plastics web.

Figure 2:
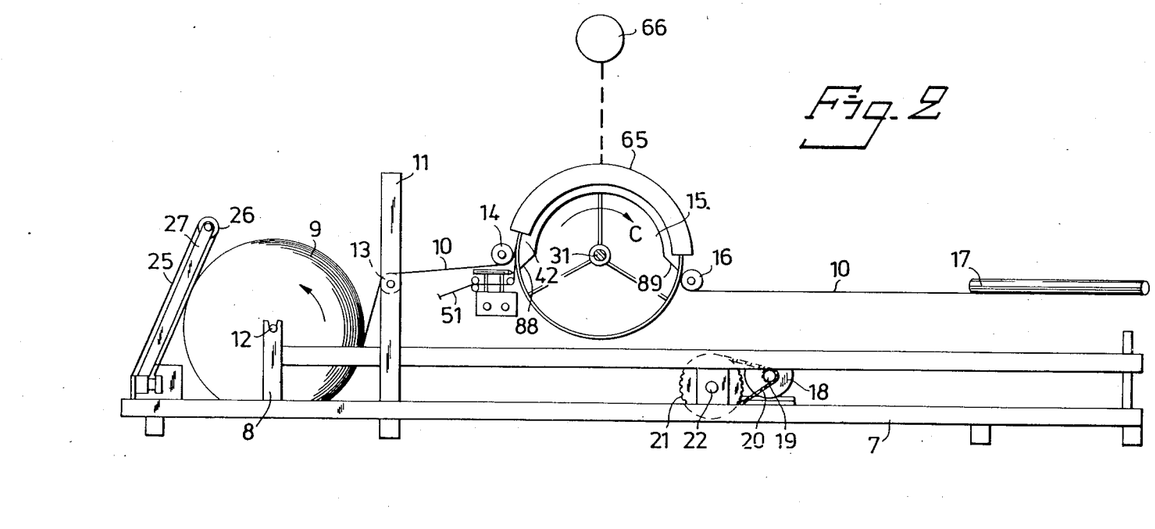
FIG. 2 illustrates in side view and in a greatly simplified manner an arrangement according to the invention with certain details omitted.

The embodiment of the invention chosen by way of example is described hereinafter with reference to FIGS. 2, 3 and 4.

Journalled in a frame structure 7 on a roll holder 8 is a roll 9 of plastics foil 10, which forms the outer layer of the finished diaper. Journalled on a frame 11 forming part of the frame structure 7 is a guide roller 13 which extends parallel to the shaft 12 of the roll 9 and over which the web 10 passes in towards and beneath a further free-running guide roller 14, which guides the web 10 upwardly and on to the peripheral surface of a drum 15 driven at a constant speed in the direction of arrow C. The guide roller 14 preferably lies against the circular-cylindrical peripheral surface of the drum 15 and presses the web against the elastically tensioned ribbon in a manner hereinafter described.

The plastics web 10 passes from the drum 15 beneath a guide roller 16, the somewhat tensioned elastic ribbons having been provided on its undersurface, from whence the web passes over a freely-rotating reversing roller 17. The web 10 then passes from the reversing roller towards a working station of well known kind, in which the elastic ribbons lie on the upper side of the plastics web. In this working station, or a sequence of working stations, there is applied a relatively thick layer of liquid-absorbent soft material, for example fluffed cellulose, together with the inner layer, whereafter the outer and inner layers are joined together and a finished diaper according to FIG. 1 for example is punched from the resultant laminate.

Figures 3, 4:
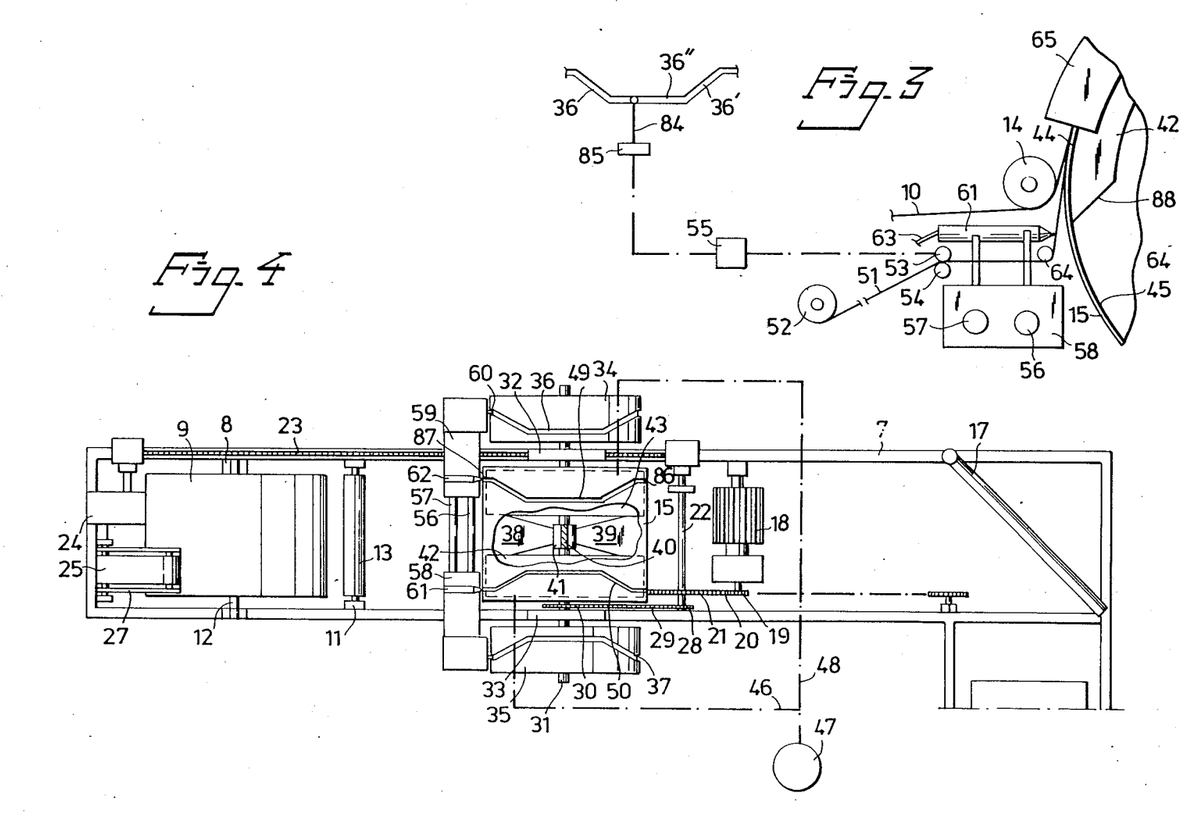
FIG. 3 illustrates a detail of the arrangement shown in FIG. 2.
FIG. 4 illustrates the arrangement of FIG. 2 as a whole, with the ribbon transfer drum partially cut away.

Mounted in the frame structure 7 is an electric motor 18 whose output shaft carries a sprocket wheel 19 which drives, via a chain 20, a further sprocket wheel 21 which is firmly mounted on a drive shaft 22 journalled in the frame structure 7 (FIG. 4). The drive shaft 22 also drives a chain 23 via a sprocket wheel (not shown) and a drive roller (not shown) for a drive belt 25, via a gearing 24, said belt extending over an upper drive roller 26 (FIG. 2). The drive rollers of the drive belt 25 are journalled on a frame 27 which can be pivoted around the lower drive roller and urged against the roll 9 carrying the plastics web with the aid of means not shown here. The drive belt 25 abutting the periphery of the roll 9 transfers a given drive force to the heavy roll 9, in order to facilitate withdrawal of the web 10 therefrom. A web take-off force is applied to the web 10 partly through the drum 15, against which the web 10 is held pressed by means of the guide rollers 14 and 16, and partly by means of drive rollers (not shown) between which the web passes and which, for example, are arranged upstream of the reversing roll 17. The drive shaft 22 is also provided with a sprocket wheel 28 (FIG. 4) which is firmly mounted on said shaft and which drives a sprocket wheel 30 via a chain 29. The sprocket wheel 30 is firmly mounted on a rotatable shaft 31 which extends transversely through the whole frame structure 7 and the end portions of which are rotatably journalled in bearing boxes located in vertical posts 32 and 33 fixed in the frame structure 7. Journalled on both ends of the shaft 31 are identical guide cylinders 34 and 35 respectively. Each guide cylinder is provided with a respective continuous cam groove 36 and 37 comprising two identical parts each including 180° of the guide cylinder. Each such groove part has a form which corresponds to the predetermined paths 49, 50 of the elastic ribbon to be attached to the plastics web 10 (cf FIG. 1) The two guide cylinders 34, 35 arranged on the outer surfaces of the frame structure 7 are firmly mounted on the shaft 31 and thus rotate synchronously with one another. It will be noted that it is assumed here that the elastic ribbons attached to both sides of the diaper in the longitudinal direction thereof lie fully symmetrically around the longitudinal axis of the diaper. Naturally, if the ribbon or ribbons on one side of the diaper are required to have a curvature which deviates from the ribbon or ribbons on the other side of said diaper, the two grooves 36 and 37 will have an appropriately differing curvature. The drum 15 is non-rotatably mounted on the shaft 31 in the frame 7 by means of robust spokes 38, 39 and 40 which extend from the center part of the drum 15 and the inner end parts of which are joined with a hub 41 securely keyed to the shaft 31. The drum 15 has open ends through which are inserted two suction boxes 42 and 43 respectively. Each suction box 42, 43 has an upper edge part 44 (cf FIG. 3) adapted to the inner surface 45 of the drum 15, said edge part 44 defining an open side of a respective box. Other sides are closed. The suction box 42 is connected to a suction source 47 via a suction pipe 46, while the suction box 43 is connected to the suction source 47 via a suction pipe 48. The suction source comprises, for example, a powerful fan or centrifugal pump adapted to create a desired subpressure in the two suction boxes 42 and 43 arranged on both sides of the carrier means 38, 39, 40 of the drum 15.

In the illustrated embodiment the peripheral surface of the drum 15 has arranged therein grooves 49 and 50 defining said predetermined paths and of the same configuration as the cam grooves 36 and 37 respectively. It is, however, emphasized that the drum can be perfectly smooth and that the elastic bands need not be fed into grooves in the surface of the drum. Each of these grooves 49 and 50 is intended to accomodate at least one elastic ribbon 51, see in particular FIG. 4, which are withdrawn from a reel 52 by means of two mutually abutting, driven rollers 53 and 54, or drawn from a box and fed in between the rollers 53, 54. The two rollers 53 and 54 are journalled in the frame structure 7 and are driven from a direct-current motor 55, as indicated in FIG. 4. Journalled in the frame structure 7 in its transverse direction are two guides 56 and 57, on which two carriages 58 and 59 can be moved. Each carriage, 58, 59, is provided with a dogging means, for example the dogging means 60 of the carriage 59, which are firmly mounted on the carriage and project into the respective allotted cam groove 36 or 37. When the shaft 31 rotates, and therewith also the drum 15 and the guide cylinders 34 and 35, the two carriages 58 and 59 are moved towards and away from each other on the two guides 56, 57. Mounted on the carriage 58 and 59 are respective adhesive nozzles 61 and 62, said nozzles being located such that their outlet orifices follow the ribbon grooves 49 and 50 during movement of the carriages. The two nozzles 61 and 62 are supplied with hot thermoplastic adhesive under pressure through conduits, for example the conduit 63 in FIG. 3 from a source not shown. Since two elastic ribbons 51 are to be withdrawn, one for each groove 49, 50, two reels 52 are provided. Each ribbon is withdrawn from its respective reel by means of the two drive rollers 53, 54 which hold the ribbon firmly there-between and feed the ribbon over a guide roller 64 into its allotted groove 49, 50. The shaft 31, and therewith the drum 15 and the guide cylinders 34, 35 are assumed here to be driven at a constant, given speed which is adapted to the rate at which work is carried out in subsequent stations. Since each elastic ribbon 51 is to be attached to the plastics web 10 in a somewhat tensioned state, and possibly under a tension which varies along the ribbon length, the rollers 53 and 54 must be driven at a speed such that the speed at which the ribbon 51 is advanced is slower than the peripheral speed of the drum 15. As will be seen from FIG. 3, subsequent to respective ribbons 51 leaving the guide roller 64 and entering their respective grooves on the drum 15 in a substantially tangential direction, adhesive is applied to the upper surface of the ribbon and the ribbon pressed by the pressure roller 14 onto the undersurface of the plastics web 10. The illustrated embodiment includes a cooling box 65 (FIG. 3) which is connected to a source 66 of cooling air and arranged above the drum 15 in order to cool the hot-melt adhesive as quickly as possible. It is also conceivable to hold the ribbon 5, which as will be understood need not be planar but may have the form of a filament of substantially circular cross-section, in the groove on the drum 15 through a distance equal to about 180°, although this distance may naturally vary, in dependence on the diameter of the drum and the length of the diaper among other factors.

Figure 5:
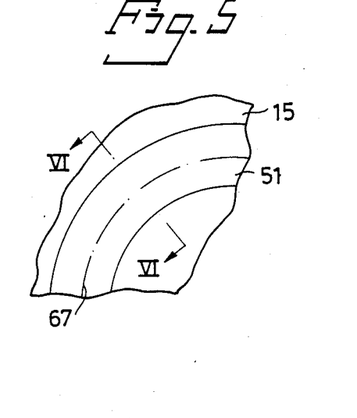
FIG. 5 illustrates part of a curved groove located on the drum periphery having a ribbon inserted in said groove, in accordance with known techniques.
Figure 6:
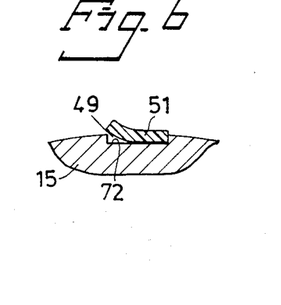
FIG. 6 is a sectional view taken on the line VI—VI in FIG. 5.

FIGS. 5 and 6 illustrate a pronounced curvature in the groove 49 and the manner in which an inserted ribbon 51 having a width exceeding its thickness behaves. The tension in the ribbon 51 is greater on the outside of the center line 67 of the groove 49 than on the inside of the center line, and as mentioned in the introduction and as illustrated in FIG. 6 the ribbon 51 will be lifted up on the outside of the curve, and in an extreme case will be rolled or tilted over the radially inward ribbon portion, resulting in poor adhesion to the plastics web 10, or in a practically negligible bond.

Figure 7:
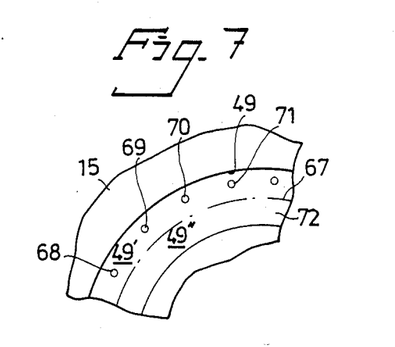
FIG. 7 illustrates part of a groove located in the drum periphery and formed in accordance with the invention.
Figure 8:
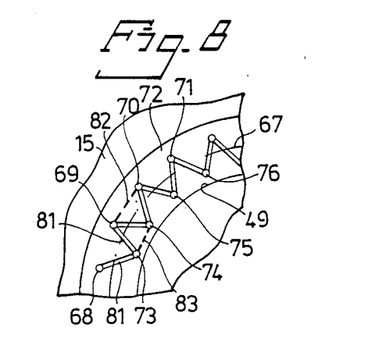
FIG. 8 illustrates a modified groove form.

The aforesaid suction boxes 42 and 43 and suction openings, for example the openings 68, 69, 70, 71 in the preferably planar bottom 72 of the grooves 49 and 50, extending substantially along the whole length of the groove (FIG. 7) are arranged in accordance with the invention to avoid this drawback. The openings 68, 69, 70, 71 communicate with the respective interiors of the suction boxes and will thus draw the nonadhesive surface of the entire ribbon 51 firmly against the groove bottom, therewith to hold the ribbon in a planar and non-slidable position in the groove. When the groove 49 is completely or partially curved as illustrated in FIG. 7, the openings must at least be arranged on the groove portion 49' (FIG. 7) distal from the center of curvature, although openings, such as the openings 73, 74, 75 and 76, are also preferably arranged on the innermost groove part 49" (FIG. 8), thereby to obtain positive retention of the edge portions of the ribbon on both sides of the center line, which further reduces the risk of the tensioned ribbon from sliding and tilting in the groove and therewith moving relative to the web 10 which moves at a constant speed. The inner and outer openings are suitably displaced relative to one another, as illustrated in FIG. 8, and in one preferred embodiment the inner and oute openings are connected with one another by means of shallow grooves, for example the grooves 80 and 81, which cross the groove bottom 72. The suction openings in the outer and inner rows respectively may be connected together directly, as illustrated by the broken lines 82 and 83 which indicate shallow grooves formed by grinding the groove bottom 72. Practical tests have shown that such grooves 82 extending in the longitudinal direction of the tape 51 between the suction openings provide a good effect with respect to preventing upward bending of the outer ribbon edge, shown in FIG. 6, while grooves 81 extending across the width of the ribbon, on the other hand, are much more effective in preventing sliding of the ribbon than the grooves 82.

This slipping or sliding of the ribbon, caused by equalization of the tension force in the ribbon, is particularly troublesome when the crotch part of a diaper is to have a more pronounced gathering than the side portions of the diaper, i.e. when the ribbons to be attached to the plastics web 10 shall have a higher degree of tension within the ultimate crotch part, corresponding to the distance G1-G2 in FIG. 1 and the corresponding distance on grooves 49, 50 than the aforesaid side parts, corresponding to the distances G1-G3 and G2-G4 respectively.

The principle by which the ribbon 51 is imparted in the illustrated embodiment with a varying tension such that the finished diaper, or some other manufactured liquid-absorbing product, has a region of greatest tension in the crotch part of the diaper is illustrated in a highly simplified manner in FIG. 3. The figure illustrates the cam grooves 36 of the guide cylinder 34, these grooves accomodating a dogging means 84, which in turn adjusts a potentiometer 85 fixedly mounted in relation to the cam groove 36. The potentiometer 85 regulates the voltage to the direct current motor 55 which drives the feed rollers 53, 54. When the setting means of the potentiometer 85 is located within the region 36', the ribbon 51 shall be imparted a continuously increasing tensile force so that when the setting means reaches the horizontal region 36" maximum tension is achieved and maintained throughout the whole of the crotch part G1-G2 (FIG. 1). This means that the outfeed speed of the feed rollers 53, 54 shall be progressively reduced within the inclined region 36', i.e. the potentiometer 85 controls the motor 55 in a manner to progressively decrease in speed until the maximum tensile force is achieved. The setting means 84 then reaches the upwardly directed part of the cam groove and the tensile force in the ribbon 51 is progressively decreased to the minimum, constantly maintained tensile force, i.e. the speed of the motor 55 is progressively increased.

Figure 11:
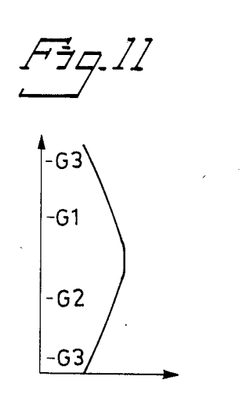
FIG. 11 is a diagram showing an example of a ribbon tension curve.

It is possible with the aid of this arrangement to vary the ribbon tension once or a number of times as the ribbon is being attached to the plastics web 10, so that the side parts of the finished products have suitably adapted forces which hold said parts together to provide the best possible seal. The ribbon tension may be given the appearance illustrated in FIG. 11, for example, in which the length markings G1-G4 shown in FIG. 1 are plotted along the Y axis and the tensile force is plotted along the X-axis. The ribbon or band is held by suction forces along its length in the predetermined curved path 49 or 50 and therefore the varying tension forces will be maintained.

Variations in tension in the ribbon 51 bonded to the web 10 may, of course, be achieved with the aid of purely mechanical means, for example, by means of an eccentric-cylinder mechanism according to the EPC-Patent Specification No. 0 027 303.

As before mentioned, these variations in tensile stress become equalized as a result of "shrinkage" of the ribbon 51 relative to the web 10 when using a groove which lacks the aforedescribed suction feature, due to the fact that the binder does not harden fully, even when an expensive hot-melt adhesive is used. When a double-sided adhesive tape is used for example, the time taken to establish a bond is so long that unless the suction technique according to the invention is applied, it is not possible to avoid sliding of the ribbon under tension. The subpressure for holding the stretched ribbon by suction is controlled automatically, so that the ribbon is captured by openings through which a suction force is exerted at the correct moment in time, and the ribbon is then released by successively removing the subpressure.

The end 86 of the upper groove part of the groove 49, and also the end 87 have been marked in FIG. 4. When the end 86 of the groove reaches the left edge part 88 (FIG. 3) of an associated suction box during rotation of the drum 15, the suction openings of the groove bottom 72 are connected with the interior of the suction box and therewith draw the end of the ribbon 51 firmly against the groove bottom, and as the drum is rotated further in a clockwise direction in FIG. 3, further suction openings will lie above the suction box and therewith cause the ribbon to be held firmly by suction along the whole of its length. When the web 10 with the elastic ribbon 51 provided with an adhesive undersurface is rotated about 180°, the original start end 86 will have reached and passed the right edge part 89 of the suction box (FIG. 2). As soon as the groove end 86 has passed this edge part, the pressure in the suction openings lying closest to the groove end 86 will lie at atmospheric pressure and the web, together with the ribbon is able to pass readily from the drum 15 and beneath the guide roller 16 while the remaining groove length lying within the suction-box opening is subjected to suction force. Thus, in practice the ribbon 51 while lying on the outer cylindrical surface of the drum 15 will be held firmly by suction at the same time as all suction effect ceases on the part of the ribbon departing from the drum, this part thus not being subjected to forces capable of pulling the ribbon loose from the web 10. As will be understood, the grooves illustrated in FIG. 8 connecting the suction openings with one another are so shallow that the ribbon material is drawn down into the grooves and seals thereagainst.

The described arrangement merely constitutes an embodiment of the invention and it will be understood that various modifications can be made without departing from the concept of the invention.

Figure 9:
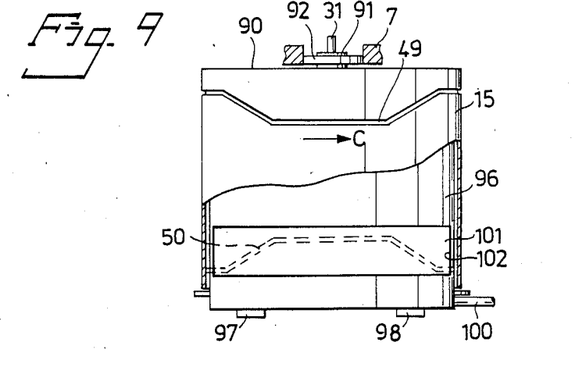
FIG. 9 illustrates a modified drum and suction means.
Figure 10:
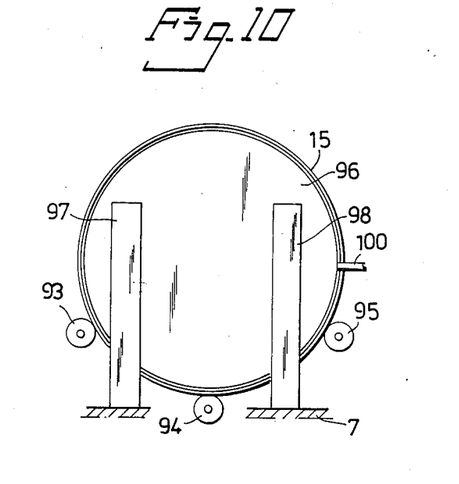
FIG. 10 illustrates the arrangement of FIG. 9, as seen towards the open end of the drum.

FIGS. 9 and 10 illustrate a modified drum having a rear side wall 90 with a hub 91 to which the drive shaft 31 is firmly connected. The hub 90 is mounted for rotation in a journal bearing 92 attached to the machine-frame structure 7 in a manner not shown. The other end part of the drum 15 is open and freely-running rollers 93, 94, 95 are journalled in the frame structure and support this end part. Inserted in the drum 15, which is shown partly in section in FIG. 9, is a cylindrical suction box 96 which extends beneath the two grooves 49, 50. The suction box 96 is carried by two bracket means 97, 98, firmly mounted to the frame structure 7.

The interior of the suction box 96 is connected to a suction source via a conduit 100. Arranged in the outer cylindrical surface of the suction box 96 are two openings which include about 180° of said outer cylindrical surface and lie in the movement paths of the grooves 49 and 50 respectively. The opening 101 for the groove 50 is shown in FIG. 9. When the drum 15 is rotated around the cylindrical, stationary suction box 96, the end edge 102 thereof will successively interrupt the connection of the holes in grooves 49, 50 will the suction source and the elastic, tensioned ribbon or filament joined to the plastics web will be released from its groove or the predetermined path on the smooth drum without requiring the application of a loosening force to the ribbon. In this case, only one guide cylinder, for example the guide cylinder 34 in FIG. 4, is assumed to be provided, while sensing of the guide curve 36 is assumed to take place with the aid of a photocell, which in turn delivers a control signal to two electric motors for guiding the two aforementioned carriages 61 and 62 towards and away from each other. As will be understood the curve 36 need not comprise a milled groove, but may comprise a track marked with a coloring agent. The requisite movements of the carriages 61 and 62 may also be effected with the aid of a data processor containing the requisite control information.

Figure 12:
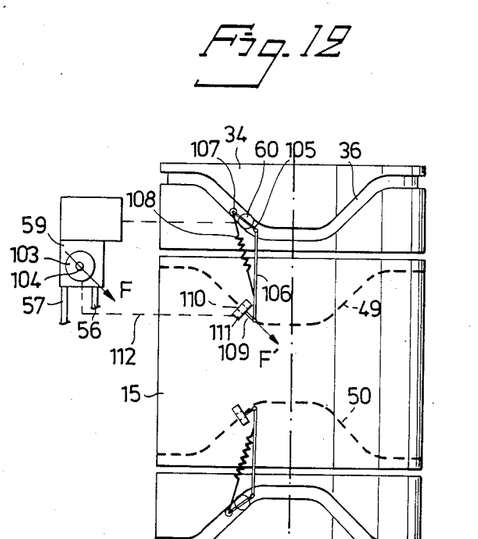
FIG. 12 illustrates a ribbon control mechanism and an associated adhesive nozzle.

When the ribbon is to be applied in a curved pattern according to the invention, for example as indicated by the grooves 49 and 50, which in the aforegoing have been assumed to have substantially the same width as the ribbon 51, an advantage is gained when the infeed of respective ribbons on the drum 15 takes place in the direction of the groove, i.e. parallel with the groove direction at the infeed location. Such infeed is, of course, also carried out when the path simply consists of a marking or imaginary path 49, 50 on a smooth drum surface. FIG. 12 illustrates schematically the principles of such an infeed, the adhesive nozzles 61 and 62 respectively also following the ribbon curves, i.e. constantly aligned with the direction of the centre line 67 (FIG. 5). FIG. 12 illustrates the one carriage 59, on which there is rotatably mounted a table 103, which is arranged for rotation about a central shaft or axis 104. The table 103 carries the adhesive nozzle 62, a guide roller 64 and drive rollers 53, 54, (FIGS. 3 and 4) and these elements will thus be rotated as a unit and determine the infeed direction of the ribbon 51 and the adhesive string, this direction being indicated in FIG. 12 by the arrow F and corresponds to the direction F' of the groove 49 at the infeed location. Although not shown, the carriage 58 (FIG. 4) is provided with a corresponding table, carrying the adhesive nozzle 61 and the ribbon-feed and ribbon-alignment rollers for the ribbon 51, which is introduced into the groove 50. FIG. 12 illustrates the dogging means 60 (FIG. 4) which, as previously described, guides the movement of carriage 59 parallel with the axis of the drum 15 and which comprises a freely rotatable wheel having a diameter corresponding to the width of the cam groove 36. The wheel 60 is rotatably journalled centrally on a pivot arm 105, one end of which is pivotably connected to a guide arm 106 and the other end of which carries a freely rotatable follower wheel 107 having a smaller diameter than the width of the cam groove 36, so that the guide means formed by the wheels 60, 107 can pass freely through curves of small radii. Arranged between the arm 105 and the arm 106 is a tension spring 108 which holds the wheel 107 pressed against the inner wall of the groove 36. The other end of the guide arm 106 is pivotably connected to a further pivot arm 109 the free end of which carries a follower wheel 110 which co-acts with the groove 49. The follower wheel 110 is journalled in a holder 111. The described and well known paralleloram-guide mechanism ensures that the rotary axis of the wheel 110 always lies at right angles to F1, and when the holder 111 is connected to the table 103 via a linkage system 112, the table 103 will thus always be adjusted in dependence on the curvature of the groove part to which ribbon and adhesive are fed at that moment in time. The table on the carriage not shown in FIG. 13 is guided with the aid of a corresponding parallelogram-link system.

As previously indicated instead of the cam grooves 36 and 37 there can be used a purely electronic guide means incorporating guide information stored in a data processor and utilized to instigate translatory movements of the carriages 58, 59 and rotational movements of the tables, for example the table 103, via drive motors.

Such electronically controlled movement is particularly suitable when the fixed paths 49, 50 are not formed by grooves provided in the outer cylindrical surface of the drum 15, but simply have the form of the described suction openings in said surface. In this case the ribbon must be placed analogously with what has been described with reference to FIG. 12, i.e. the position of the ribbon at the point of application must, at each moment in time, correspond to the determined shape of the path 49 and 50 respectively.

I claim:

1. An apparatus for bonding a tensioned elastic ribbon (51) with the aid of an adhesive along a given path (49,50) on a plastics web (10) in the manufacture of diapers or like liquid-absorbing products, the apparatus comprising: a rotatable cylindrical drum (15) for receiving the ribbon along a predetermined path (49,50) on the drum in correspondence with the given path (49,50); feed-in means for delivering the ribbon onto said drum; means (18,19,29,30) for rotatably driving the drum; means for contacting the ribbon with the plastics web (10) along a given distance on the peripheral surface of the drum; means for retaining the ribbon in its position on the peripheral surface of the drum, the retaining means including suction openings provided along the predetermined path on the drum, and a suction source in communication with the suction openings; means (89,102) for breaking the communication between the suction openings and the suction source as a respective suction opening completes its passage along a distance at least equal to the given distance on the peripheral surface,
wherein the given path (49,50) follows a curved line, and the apparatus further comprises means (36,37,58,59) for guiding the ribbon (51) along the peripheral surface of the drum (15) and in the axial direction of the drum in correspondence with the curvature of the predetermined path, the suction openings being distributed along substantially the whole of the length of the predetermined path,
whereby different portions of the ribbon corresponding to different portions of the predetermined path are subjected to, and maintained at, different tensions.

2. An apparatus according to claim 1, wherein: the predetermined path is defined by a groove (49,50) on the peripheral surface of the drum (15); and the suction openings (68–71; 73–76) are located in the bottom (72) of the groove.

3. An apparatus according to claim 1 wherein the suction openings (68–71) are located on one side of the center line (67) of the predetermined path.

4. An apparatus according to claim 1, wherein the openings (68–71; 73–76) are arranged on both sides of the center line (67) of the predetermined path.

5. An apparatus according to any one of claims 1–4, wherein the suction source includes a suction box (42,43,96) which is stationarily arranged beneath the predetermined path and in the interior of the drum (15), the suction box being communicated with a fan (47) or like means for creating suction, and the suction box being provided with an opening (101) having a length in the peripheral direction of the drum (15) corresponding to the given distance.

6. An apparatus according to claim 5, wherein one end edge (89,102) of the opening in the suction box (42,43,96) forms the means (89,102) for breaking the communication between the suction openings and the suction source.

7. An apparatus according to any one of claims 1–4, the apparatus further comprising guide means (64,103,60,105,106,107,109,110) for aligning the ribbon parallel with the direction of the predetermined path (49,50) at the ribbon infeed location on the drum (15).

8. An apparatus according to claim 7, wherein the ribbon is provided with a string of adhesive with the aid of an adhesive nozzle (61,62), and the guide means includes means for aligning the adhesive nozzle parallel with the direction of the predetermined path at the ribbon infeed location on the drum (15).

9. An apparatus according to claim 2, wherein the suction openings (68–71) are located on one side of the center lin (67) of the predetermined path.

10. An apparatus according to claim 2, wherein the openings (68,71; 73–76) are arranged on both sides of the center line (67) of the predetermined path.

11. An apparatus according to claim 5, wherein the apparatus further comprises guide means (64,103,60,105–107,109 and 110) for aligning the ribbon parallel with the direction of the predetermined path (49,50) at the ribbon infeed location on the drum (15).

12. An apparatus according to claim 11, wherein the ribbon is provided with a string of adhesive with the aid of an adhesive nozzle (61,62), and the guide means includes means for aligning the adhesive nozzle parallel with the direction of the predetermined path at the ribbon infeed location on the drum (15).

13. An apparatus according to claim 6, wherein the apparatus further comprises:
guide means (64,103,60,105,106,107,109,110) for aligning the ribbon parallel with the direction of the predetermined path (49,50) at the ribbon infeed location on the drum (15).

14. An apparatus according to claim 13, wherein the ribbon is provided with a string of adhesive with the aid of an adhesive nozzle (61,62), and the guide means includes means for aligning the adhesive nozzle parallel with the direction of the predetermined path at the ribbon infeed location on the drum (15).

15. An apparatus for bonding a tensioned elastic ribbon (51) with the aid of an adhesive along a given path (49,50) on a plastics web (10) in the manufacture of diapers or like liquid-absorbing products, the apparatus comprising: a rotatable cylindrical drum (15) for receiving the ribbon along a predetermined path (49,50) on the drum in correspondence with the given path (49,50); feed-in means for delivering the ribbon onto said drum; means (18,19,29,30) for rotatably driving the drum; means for contacting the ribbon with the plastics web (10) along a given distance on the peripheral surface of the drum; means for retaining the ribbon in its position on the peripheral surface of the drum and for maintaining a variable tension over the length of the ribbon positioned on the drum, the retaining and maintaining means including suction openings provided along the predetermined path on the drum, and a suction source in communication with the suction openings; means (89,102) for breaking the communication between the suction openings and the suction source as a respective suction opening completes its passage along a distance at least equal to the given distance on the peripheral surface, wherein the given path (49,50) follows a curved line, and the apparatus further comprises means (36,37,58,59) for guiding the ribbon (51) along the peripheral surface of the drum (15) and in the axial direction of the drum in correspondence with the curvature of the predetermined path, the suction openings being distributed along substantially the whole of the length of the predetermined path, whereby different portions of the ribbon corresponding to different portions of the predetermined path are subjected to, and maintained at, different tensions.

16. An apparatus according to claim 15, wherein the ribbon has a substantially rectangular cross-section.

* * * * *